(12) United States Patent
Ye et al.

(10) Patent No.: US 7,666,650 B2
(45) Date of Patent: Feb. 23, 2010

(54) AMYLASE

(75) Inventors: Liu Ye, Beijing (CN); Tang Lan, Beijing (CN); Tina Spendler, Malov (DK); Mary Ann Stringer, Soborg (DK)

(73) Assignee: NovoZymes A/S, Bagsvaerd (DK)

( * ) Notice: Subject to any disclaimer, the term of this patent is extended or adjusted under 35 U.S.C. 154(b) by 219 days.

(21) Appl. No.: 10/585,620

(22) PCT Filed: Dec. 22, 2004

(86) PCT No.: PCT/DK2004/000896

§ 371 (c)(1),
(2), (4) Date: Jul. 8, 2006

(87) PCT Pub. No.: WO2005/066338

PCT Pub. Date: Jul. 2, 2005

(65) Prior Publication Data

US 2007/0166432 A1    Jul. 19, 2007

Related U.S. Application Data

(60) Provisional application No. 60/535,112, filed on Jan. 8, 2004.

(30) Foreign Application Priority Data

Jan. 8, 2004    (DK)    ............................... 2004 00021

(51) Int. Cl.
| | |
|---|---|
| C12N 9/30 | (2006.01) |
| C12N 9/26 | (2006.01) |
| C12N 1/20 | (2006.01) |
| C12N 15/20 | (2006.01) |
| C12P 21/06 | (2006.01) |
| A21D 2/00 | (2006.01) |
| C07H 21/04 | (2006.01) |

(52) U.S. Cl. ...................... 435/203; 435/201; 435/69.1; 435/320.1; 435/252.33; 435/252.3; 426/20; 536/23.1; 536/23.2

(58) Field of Classification Search ........................ None
See application file for complete search history.

(56) References Cited

FOREIGN PATENT DOCUMENTS

| WO | WO 91/04669 | 4/1991 |
|---|---|---|
| WO | WO 96/01323 | 1/1996 |
| WO | WO 00/59307 | 3/2000 |
| WO | WO 03/016535 | 2/2003 |
| WO | WO 03/083054 | 10/2003 |

OTHER PUBLICATIONS

Brown T., Hybridization analysis of DNA blots. Current Protocols in Moelcular Biology, Unit 2.10: 2.10.12.10.16, 1993, Published by John Wiley & Sons, USA.*
Guo et al., Protein tolerance to random amino acid change. PNAS., 2004, vol. 101: 9205-9210. Published online Jun. 14, 2004.*
Whisstock et al., Prediction of protein function from protein sequence. Q. Rev. Biophysics., 2003, vol. 36 (3): 307-340.*
Broun et al., Catalytic plasticity of fatty acid modification enzymes underlying chemical diversity of plant lipids. Science. 1998, vol. 282: 1315-1317.*
Witkowski et al., Conversion of b-ketoacyl synthase to a malonyl decarboxylase by replacemnt of the active-site cysteine with glutamine. Biochemistry, 1999, vol. 38: 11643-11650.*
Seffernick et al., Melamine deaminase and Atrazine chlorohydrolase: 98 percent identical but functionally different. J. Bacteriol.,2001, vol. 183 (8): 2405-2410.*
Swift, HJ et al, Structure and Molecular Model Refinement of *Aspergillus oryzae* (Taka) Alpha-Amylase: and Application of the Simulted-Annealing Method, (1992), RCSB Protein Data Bank Aug. 1, 2004.
Gupta et al, Microbial Alpha-Amylase: A Biotechnological Perspective, vol. 38, Part 11, pp. 1599-1616 (2003).

* cited by examiner

*Primary Examiner*—Ganapathirama Raghu
(74) *Attorney, Agent, or Firm*—Elias J. Lambiris; Kristin J. McNamara

(57) ABSTRACT

The inventors have identified amylases in fungal strains of *Valsaria* and found that the amylase can increase the shelf life of baked products. Particularly, the novel amylase in combination with a maltogenic amylase further improves the softness of bread crumb without having detrimental effects on elasticity.

14 Claims, No Drawings

AMYLASE

CROSS-REFERENCE TO RELATED APPLICATIONS

This application is a 35 U.S.C. 371 national application of PCT/DK2004/000896 filed Dec. 22, 2004, which claims priority or the benefit under 35 U.S.C. 119 of Danish application No. PA 2004 00021 filed Jan. 8, 2004 and U.S. provisional application No. 60/535,112 filed Jan. 8, 2004, the contents of which are fully incorporated herein by reference.

FIELD OF THE INVENTION

The present invention relates to amylases and their addition to dough to prevent staling of dough-based products.

BACKGROUND OF THE INVENTION

Endo-amylases are often added to dough to make the dough more soft and to improve the moistness, often in combination with an exo-amylase, e.g. a maltogenic alpha-amylase. However, the addition of endo-amylases of bacterial origin, e.g. *B. amyloliquefaciens* amylase easily gives a risk of overdosing, giving loss of elasticity and a too gummy crumb. Fungal amylases are often added to dough, but they only provide little effect on the softness A fungal amylase (Taka amylase) from *Aspergillus oryzae* is described in Pdb file 6taa (available at www.rcsb.org).

SUMMARY OF THE INVENTION

The inventors have identified an amylase in fungal strains of *Valsaria* and found that the amylase can increase the shelf life of baked products. Particularly, the novel amylase in combination with an exo-amylase further improves the anti-staling effect of the exo-amylase. The improved anti-staling may be an improved the softness of bread crumb without a detrimental effect on crumb elasticity or even with an improved elasticity.

The amino acid sequence of the novel amylase was found to include a catalytic domain and a carbohydrate-binding domain (CBM), each of which can be used separately. Accordingly, the invention provides a polypeptide with a sequence including a catalytic core and a polypeptide with a sequence including a carbohydrate-binding domain (CBM).

The novel amylase is thermostable, and the inventors found that a combination of two amylases can be used for anti-staling, where one is a thermostable amylase (particularly a fungal amylase) which includes both a catalytic core and a CBM, and the other is an exo-amylase.

The invention also provides a polypeptide having an amino acid sequence which can be obtained from the mature polypeptide (particularly the catalytic coreof SEQ ID NO: 2 or 19 by substitution, deletion, and/or insertion of one or more amino acids and a polynucleotide having a sequence that can be derived from SEQ ID NO: 1 or 18 by substitution, deletion, and/or insertion of one or more nucleotides.

The invention also provides a polynucleotide encoding the amylase, an expression vector comprising the polynucleotide, a transformed host cell comprising the vector, as well as a method of producing the amylase by cultivating the transformant. The invention further provides a dough composition comprising the amylase, a method of preparing a dough-based product by leavening and heating the dough, e.g. by baking.

DETAILED DESCRIPTION OF THE INVENTION

Genomic DNA Source

A source organism of the amylase of the invention is a fungal strain isolated from soil samples collected from Hainan Province, China, in 2002. The strain was at first classified as *Chaetomium* sp. and was later re-classified as *Valsaria rubricosa* belonging to Diaporthales, Ascomycetes, Ascomycota. It was found to harbor an amylase gene shown in SEQ NO: 1. The inventors have cloned the gene into a strain of *E. coli* and deposited it under the terms of the Budapest Treaty on 16 Dec. 2003 as DSM 16113 with the DSMZ—Deutsche Sammlung von Microorganismen und Zellkulturen GmbH, Mascheroder Weg 1b, D-38124 Braunschweig DE.

The inventors also found an amylase gene in *Valsaria rubricosa* CBS 848.96. This strain is available on commercial terms from Centraalbureau voor Schimmelcultures, Uppsalalaan 8, P.O. Box 85167, 3584 CT, The Netherlands, *Valsaria rubricosa* CBS 848.96 was found to harbor an amylase gene shown in SEQ NO: 18

Polypeptide with Amylase Activity

The polypeptide with amylase activity has an amino acid sequence which includes a catalytic core which may be the catalytic core sequence encoded by a DNA sequence in a plasmid present in *E. coli* DSM 16113, the sequence shown in positions 1-439 of SEQ ID NO 2, or a sequence having at least 70% identity to said sequences. Also, the catalytic core may be a sequence encoded by a nucleic acid sequence which hybridizes at 55° C. with the complementary strand of nucleotides 146-1462 of SEQ ID NO: 1.

Optionally, the amino acid sequence may further comprise both the catalytic domain and a carbohydrate-binding module (CBM), or it may include the catalytic domain without a CBM. The CBM may be that present in the donor strain or an analogue thereof, or an extrinsic CBM may be substituted, or one or more additional CBMs may be inserted.

The polypeptide may have the sequence shown as SEQ ID NO: 19.

Carbohydrate-Binding Domain (CBM)

The carbohydrate-binding module (CBM) or carbohydrate-binding domain (CBD) is a polypeptide which binds preferentially to a poly- or oligosaccharide (carbohydrate), particularly in water-insoluble (e.g. crystalline) form. It may particularly be a starch-binding modules (SBM) or starch-binding domain (SBD). The one or more CBMs may optionally further comprise one or more polypeptide amino acid sequence regions linking the CBM(s) with the catalytic module(s), a region of the latter type usually being denoted a "linker".

The invention provides a polypeptide with an amino acid sequence including a CBM with at least 70% identity to amino acids 440-566 of SEQ ID NO: 2.

Heterologous Carbohydrate-Binding Modules

The CBM per se typically consists of more than about 30 and less than about 250 amino acid residues. The CBM may be a "Carbohydrate-Binding Module of Family 20" or a CBM-20 module, typically a sequence of approximately 100 amino acids having at least 45% homology to the Carbohydrate-Binding Module (CBM) of the polypeptide disclosed in FIG. 1 by Joergensen et al (1997) in Biotechnol. Lett. 19:1027-1031, where the CBM comprises the last 102 amino acids of the polypeptide, i.e. the subsequence from amino acid 582 to amino acid 683.

The CBM (or SBM) may be derived from a starch degrading enzyme (amylolytic enzyme), such as a glucoamylase (EC 3.2.1.3), a cyclodextrin glucanotransferases or CGTase (EC 2.4.1.19), an alpha-amylase (EC 3.2.1.1) or a maltogenic alpha-amylase (EC 3.2.1.133). The CBM may be derived from fungal, bacterial or plant sources, e.g. derived from *Aspergillus* sp., *Bacillus* sp., *Klebsiella* sp., or *Rhizopus* sp. The CBM may also be in the form of a non-hydrolytic polysaccharide-binding protein, e.g. found in algae, such as red alga *Porphyra purpurea*. The CBM may be located at the N or C terminus or at an internal position in a polypeptide (e.g. an enzyme).

Further examples of CBMs are described in PCT/US2004/020499, incorporated herein by reference.

Combination of Amylases

A combination of two amylases may be added to dough to achieve anti-staling in a product made from the dough.

The first amylase may be a thermostable amylase which includes a CBM, particularly a fungal amylase. It may be an alpha-amylase which retains more than 50% activity after 15 min incubation at 62° C. (or 64° C. or 66° C.) in 50 mM sodium acetate, 1 mM CaCl2, pH 5.7. It may have less than 50% activity at 71° C. (or 69° C.) under the same conditions. An example is the *Valsaria* amylase described above.

The second amylase may be an exo-amylase. It may be capable of hydrolyzing starch by cleaving off linear maltooligosaccharides, e.g. maltose, maltotriose or maltotetraose, from the non-reducing ends of amylopectin. One example is maltogenic alpha-amylase (EC 3.2.1.133) such as Novamyl® or a variant thereof, e.g. having at least 90% amino acid identity to Novamyl as described in U.S. Pat. No. 6,162,628, where the Novamyl sequence is shown as SEQ ID NO: 1.

The exo-amylase may hydrolyze amylose (e.g. wheat amylose or synthetic amylose) so that the average molecular weight of the amylose after 0.4-4% hydrolysis (i.e. between 0.4-4% hydrolysis of the total number of bonds) is more than 50% (particularly more than 75%) of the value before the hydrolysis. The hydrolysis can be conducted at the conditions described above, and the molecular weight distribution before and after the hydrolysis can be determined by HPLC. The test may be carried out as described in C. Christophersen et al., Starch 50 (1), 39-45 (1998).

Recombinant Expression Vector

The expression vector of the invention typically includes a selectable marker and control sequences encoding a promoter, a 5' untranslated leader and, a transcription terminator. The vector may be an autonomously replicating vector, or it may be integrated into the host cell genome.

Production by Cultivation of Transformant

The polypeptide of the invention may be produced by transforming a suitable host cell with a DNA sequence encoding the amylase, cultivating the transformed organism under conditions permitting the production of the enzyme, and recovering the enzyme from the culture.

The host organism may particularly be a eukaryotic cell, in particular a fungal cell, such as a yeast cell or a filamentous fungal cell, e.g. a strain of *Aspergillus, Fusarium, Trichoderma* or *Saccharomyces,* particularly *A. niger, A. oryzae, F. graminearum* or *S. cerevisiae.*

Hybridization

Suitable conditions for determining hybridization between a nucleotide probe and a homologous DNA or RNA sequence involve presoaking of the filter containing the DNA fragments or RNA to hybridize in 5×SSC (standard saline citrate) for 10 min, and prehybridization of the filter in a solution of 5×SSC (Sambrook et al. 1989), 5×Denhardt's solution (Sambrook et al. 1989), 0.5% SDS and 100 µg/ml of denatured sonicated salmon sperm DNA (Sambrook et al. 1989), followed by hybridization in the same solution containing a random-primed (Feinberg, A. P. and Vogelstein, B. (1983) *Anal. Biochem.* 132:6-13), $^{32}$P-dCTP-labeled (specific activity>1×10$^9$ cpm/µg ) probe for 12 hours at approx. 45° C. The filter is then washed two times for 30 minutes in 2×SSC, 0.5% SDS at a temperature of at least 55° C., more particularly at least 60° C., more particularly at least 65° C., even more particularly at least 70° C., especially at least 75° C. Molecules to which the oligonucleotide probe hybridizes under these conditions may be detected using a x-ray film.

Alignment and Identity

The polypeptide and polynucleotide of the invention may have identities to the disclosed sequences of at least 80%, particularly at least 85% or at least 90%, e.g. at least 95%.

For purposes of the present invention, alignments of sequences and calculation of identity scores may be done using a Needleman-Wunsch alignment (i.e. global alignment), useful for both protein and DNA alignments. The default scoring matrices BLOSUM50 and the identity matrix are used for protein and DNA alignments respectively. The penalty for the first residue in a gap is −12 for proteins and −16 for DNA, while the penalty for additional residues in a gap is −2 for proteins and −4 for DNA. Alignment is from the FASTA package version v20u6 (W. R. Pearson and D. J. Lipman (1988), "Improved Tools for Biological Sequence Analysis", PNAS 85:2444-2448, and W. R. Pearson (1990) "Rapid and Sensitive Sequence Comparison with FASTP and FASTA", Methods in Enzymology, 183:63-98).

Dough

The dough of the invention generally comprises flour, particularly wheat flour. The dough may be fresh, frozen or par-baked. It may be a laminated dough.

The dough may also comprise other conventional dough ingredients, e.g.: proteins, such as milk powder and gluten; eggs (either whole eggs, egg yolks or egg whites); an oxidant such as ascorbic acid, potassium bromate, potassium iodate, azodicarbonamide (ADA) or ammonium persulfate; an amino acid such as L-cysteine; a sugar; a salt such as sodium chloride, calcium acetate, sodium sulfate or calcium sulfate. The dough may comprise fat (triglyceride) such as granulated fat or shortening.

Additional Enzyme

Optionally, one or more additional enzymes may be added to the dough together with the amylase(s) described above. The additional enzyme may be a lipolytic enzyme (e.g. as described in WO 9953769) or a xylanase.

Dough-Based Product

The invention provides a method for preparing a dough-based product by leavening the dough and heating it, e.g. by baking or steaming. The dough may be leavened e.g. by adding chemical leavening agents or yeast, usually *Saccharomyces cerevisiae* (baker's yeast). The product may be of a soft or a crisp character, either of a white, light or dark type. Examples are steamed or baked bread (in particular white, whole-meal or rye bread), typically in the form of loaves or rolls.

Amylase Units (AmU)

Amylase activity was assayed by incubating with Phadebas amylase test tablets (product of Amersham Pharmacia) suspended in 50 mM sodium acetate +1 mM CaCl$_2$ at pH 5.7 and determining OD at 650 nm. The Amylase Unit (AmU) was defined by taking the activity of the commercial product BAN 480L (product of Novozymes A/S) as 480 AmU.

EXAMPLES

Materials and Methods

RNeasy Mini Kit (Qiagen, Cat. #74904).
Taq DNA polymerase (Promega, Cat. # M166A)
pGEM-T Vector System I (Promega, Cat. # A3600)
Wizard Plus Minipreps DNA Purification System (Promega, Cat. # A7510)
5' Rapid Amplifiction of cDNA End System (Life Technologies, 5'RACE, Cat. # 18374-041),
3' Rapid Amplifiction of cDNA End System (Life Technologies, 3' RACE, Cat. # 1085805)
ElectroMAX DH10B Cells (Life Technologies, Cat. # 18290-015)

Example 1

Cultivation of Fungal Strain for cDNA Preparation

A fungal strain of *Valsaria rubricosa* was grown on YG agar plate (4.5 cm diam) for 5 days under 37° C. in the darkness and used for inoculating shake flask. The plates with fully grown cultures were stored at 4° C. before use.

To obtain the mycelium for cDNA library construction, 4-6 agar plugs with fully grown fungal cultures on the YG agar plates were used to inoculate one shake flask with FG-4 (50 ml in 500 ml Erlenmeyer flask with 2 baffles: 30 g Soymeal, 15 g Maltose, 5 g Peptone, 1000 ml $H_2O$, 1% starch, 1 g olive oil (2 drops/flask); Autoclave at 121° C. for 30 min) and grown under 37° C., 160 rpm for 24 hours. The mycelium was harvested by centrifugation of the culture broth at 8000 rpm and 4° C. for 30 minutes. Then mycelium was transferred into a clean plastic bag following by immediately freezing in liquid nitrogen and stored at −80° C. before total RNA was isolated.

Probe Designing:

Degenerate primers were designed based on alignment of already known amylase gene sequences: amyD1 (SEQ ID NO: 3) and amyD2R (SEQ ID NO: 4).

The N-terminal amino acid sequence of the purified amylase AM835F was determined as shown in SEQ ID NO: 13. This was used to design four degenerate primers: AM835n-s1 (SEQ ID NO: 5), AM835n-s2a (SEQ ID NO: 6), AM835n-s2b (SEQ ID NO: 7), AM835n-s2c (SEQ ID NO: 8).

Extraction of Total RNA:

Total RNA was isolated from the frozen mycelium of a strain of *Valsaria rubricosa* by using RNeasy Mini Kit according to the manufacturer's instructions.

Gene Cloning:

cDNA was synthesized using 3' RACE kit. The primary PCR was performed by using N-terminal based degenerate primers (primer AM835n-s2 is a mixture of AM835n-s2a, b and c) with AUAP provided by the 3'RACE kit:

| | |
|---|---|
| 10× PCR buffer | 5 micro-l |
| 25 mM MgCl2 | 3 micro-l |
| 10 mM dNTP | 1 micro-l |
| 100 micro-M AM835n-s2a | 1 micro-l |
| 100 micro-M AM835n-s2b | 1 micro-l |
| 100 micro-M AM835n-s2c | 1 micro-l |
| AUAP | 1 micro-l |
| cDNA | 2 micro-l |
| Taq DNA polymerase (5 u/micro-l) | 1 micro-l |
| $H_2O$ | 34 micro-l |

The PCR program was: 94° C. for 3 min; 30 cycles of 94° C. for 30s, 50° C. for 30s, 72° C. for 1.5 min; final extension at 72° C. for 10 min.

There was no specific amplification seen when the PCR product was visualized under UV but this product was used for second PCR with degenerate primers designed based on amylase homology. The $2^{nd}$ PCR was performed by using amylase probes (amyD1 and amyD2R) and using the primary PCR as template:

| | |
|---|---|
| 10× PCR buffer | 5 micro-l |
| 25 mM MgCl2 | 3 micro-l |
| 10 mM dNTP | 1 micro-l |
| 100 micro-M amyD1 | 1 micro-l |
| 100 micro-M amy D2R | 1 micro-l |
| $1^{st}$ PCR | 1 micro-l |
| Taq DNA polymerase (5 u/micro-l) | 1 micro-l |
| $H_2O$ | 37 micro-l |

The PCR program was: 94° C. for 3 min; 30 cycles of 94° C. for 30s, 50° C. for 30s, 72° C. for 1 min; final extension at 72° C. for 10 min. A specific band was amplified at ~700 bps and this was confirmed to be amylase by sequencing.

Based on the above obtained partial sequence, new primers were designed for 5' and 3' end cloning. For 5' end cloning, after cDNA was synthesized initiated with amy835as1 (SEQ ID NO: 9) by 5'RACE kit, PCR was performed with primer pairs amy835as1 and AAP (provided by the kit). Then nested PCR was performed with primer pair amy835as3 (SEQ ID NO: 14) and AUAP by using primary PCR (amy835as1-AAP) as template. A fragment of ~600 bp was obtained and confirmed by sequencing. For 3' end cloning, PCR was performed by using primer pair of amy835f1 (SEQ ID NO: 15) and AUAP and cDNA as template. The nested PCR was performed by using primer pair amy835f2 (SEQ ID NO: 10) with AUAP and $1^{st}$ PCR as template. A fragment at ~600 bps was amplified and again confirmed by sequencing.

Then based on the cloned 5' and 3' end sequences, the 5' and 3' end primers for full length cloning was designed and used for full length cloning of the amylase AM835. By using cDNA synthesized by 3' RACE kit as template and probes amy835s00 (SEQ ID NO: 11) and amy835as01 (SEQ ID NO: 12) as primers:

| | |
|---|---|
| 10× PCR buffer | 5 micro-l |
| 25 mM MgCl2 | 3 micro-l |
| 10 mM dNTP | 1 micro-l |
| 10 micro-M amy835s00 | 1 micro-l |
| 10 micro-M amy835as01 | 1 micro-l |
| cDNA | 2 micro-l |
| Taq DNA polymerase (5 u/micro-l) | 1 micro-l |
| $H_2O$ | 36 micro-l |

PCR program was: 94° C. for 3 min; 30 cycles of 94° C. for 30s, 50° C. for 30s, 72° C. for 1.5 min; final extension at 72° C. for 10 min.

A specific fragment of ~2.0 kb was PCR-amplified. The fragment was cloned into pGEM-T vector (Promega) which has a 3'-T overhang and transformed into *E. coli* DH10B (ElectroMAX DH10B Cells, available from Life Technologies, Cat. # 18290-015) and further sequenced.

Example 2

Production of Amylase

YG and FG-4 media were prepared as follows:

YG: Yeast-glucose agar

| | |
|---|---|
| 5.0 g Difco powdered yeast extract; | 10.0 g glucose |
| 20.0 g agar; | 1000 ml tap water |
| Autoclave at 121° C. for 15-20 min. | |
| FG-4 Media 50 ml/flask: | |
| 30 g Soymeal, | 15 g Maltose |
| 5 g Peptone, | 1000 ml H$_2$O |
| 1 g olive oil (2 drops/flask) | |
| 50 ml in 500 ml Erlenmeyer flask with 2 baffles. | |
| Autoclave at 121° C. for 30 min. | |

A strain of the thermophilic fungus *Valsaria rubricosa* was grown on YG agar plate (4.5 cm diam) for 3 days under 37° C. in the darkness and used for inoculating shake flask. The plates with fully grown cultures were stored at 4° C. before use.

For enzyme production, 4-6 agar plugs with fully grown fungal cultures on the above plates were used to inoculate one shake flask with FG-4 and grown under 37° C., 160 rpm for 72 hours, then harvested by centrifuged the culture broth at 8000 rpm and 4° C. for 30 minutes. The supernatant was collected and used for enzyme purification.

1000 ml supernatant was precipitated with ammonium sulfate (80% saturation) and redissolved in 100 ml 25 mM Tris-HCl buffer, pH7.0, then dialyzed against the same buffer and filtered through a 0.45 mm filter, the final volume was 200 ml. The solution was applied to a 35 ml Source 15Q column (Pharmacia) equilibrated in 25 mM Tris-HCl buffer, pH7.0, and the proteins was eluted with a linear NaCl gradient (0-0.3M). Fractions from the column were analyzed for amylase activity on AZCL-amylose at pH 5.5. Fractions with amylase activity were pooled. Then the pooled solution was ultrafiltrated, the concentrated solution was applied to a 180 ml Superdex75 column equilibrated with 25 mM Tris-HCl, pH7.0, the proteins was eluted with the same buffer. Amylase containing fractions were analyzed by SDS-PAGE and pure fractions were pooled.

The purified amylase was used for characterization in the following example.

Example 3

Expression of an Amylase from *Valsaria rubricosa* in *Aspergillus oryzae*

The DNA sequence of the *Valsaria rubricosa* amylase (SEQ ID NO.: 1) was used to design primers for PCR amplification of the amylase encoding-gene from the clone described in Example 1, with appropriate restriction sites added to the primer ends to facilitate sub-cloning of the PCR product (primers AM835.1 and AM835.2, SEQ ID NO: 16 and 17). PCR amplification was performed using AmpliTaq Gold DNA Polymerase (Applied Biosystems, Foster City, Calif., USA) following the manufacturer's instructions and using an annealing temperature of 55° C. for the first 5 cycles and 65° C. for an additional 25 cycles and an extension time of 2 minutes.

The PCR fragment was restricted with BamHI and XhoI and cloned into the *Aspergillus* expression vector pMStr57 using standard techniques. The expression vector pMStr57 contains the same elements as pCaHj483 (WO 98/00529), with minor modifications made to the *Aspergillus* NA2 promoter as described for the vector pMT2188 in WO 01/12794, and has sequences for selection and propogation in *E. coli*, and selection and expression in *Aspergillus*. Specifically, selection in *Aspergillus* is facilitated by the amdS gene of *Aspergillus nidulans*, which allows the use of acetamide as a sole nitrogen source. Expression in *Aspergillus* is mediated by a modified neutral amylase II (NA2) promoter from *Aspergillus niger* which is fused to the 5' leader sequence of the triose phosphate isomerase (tpi) encoding-gene from *Aspergillus nidulans*, and the terminator from the amyloglucosidase-encoding gene from *Aspergillus niger*. The amylase-encoding gene of the resulting *Aspergillus* expression construct, pMStr91, was sequenced and the sequence agreed completely with that determined previously.

The *Aspergillus oryzae* strain BECh2 (WO 00/39322) was transformed with pMStr91 using standard techniques (Christensen, T. et al., (1988), Biotechnology 6, 1419-1422). Transformants were cultured in YP+2% G medium shaken at 250 RPM at 30° C. and expression of amylase was monitored by SDS-PAGE.

Medium YP+2% G
  10 g yeast extract
  20 g peptone
  water to 1 L
  autoclave at 121° C., 20 minutes
  add 100 ml 20% sterile glucose solution

Example 4

Characterization of Amylase

The molecular weight of the amylase prepared in a previous example was found to be around 66 kDa as seen on SDS-PAGE. The isoelectric point (pI) was found to be around pH 3.5, as determined by isoelectric focusing (IEF).

pH and temperature profiles were determined with AZCL-amylose (product of Megazyme) as substrate. At 50° C., the amylase was found to be active at pH 4-10 with an optimum around pH 5-7. At pH 5.5, the amylase was found to be active at 20-70° C. with an optimum around 60° C. Thus, the *Valsaria rubricosa* amylase has a wider pH range and a higher temperature optimum than the fungal amylase from *Aspergillus oryzae*.

Stability of the amylase was determined by incubation at pH 5-7 and 60-80° C. for 5-25 minutes. The results showed more than 90% residual activity after 20 minutes at pH 6-7 and 60° C. At pH 5.0 and 60° C., the amylase was nearly completely inactivated in 15 minutes. At 70° C., the amylase was nearly completely inactivated at in 5-10 minutes at pH 6-7. It was found that at all conditions the *Valsaria rubricosa* amylase is more stable than the fungal amylase from *Aspergillus oryzae*.

The amylase showed no activity on the following substrates at pH 7.0: AZCL-galactomannan, AZCL-beta-glucan, AZCL-dextran, AZCL-xyloglucan, AZCL-potato galactan, AZCL-arabinan, AZCL-pullulan, AZCL-xylan, AZCL-hecellulose and AZCL-casein.

Example 5

Effect of Amylase on Freshness of Bread

Bread were baked according to the sponge & dough method.

| Recipes | |
|---|---|
| | % on flour basis |
| Sponge | |
| Soya oil | 2.5 |
| Sodium stearoyl lactylate (SSL) | 0.38 |
| Yeast | 5 |
| Wheat flour | 60 |
| Water | 62 |
| Dough | |
| Ascorbic acid | optimized for each flour |
| ADA | 20 ppm |
| Salt | 2 |
| Syrup | 7 (dry substance) |
| Water | optimized for each flour |
| Wheat flour | 40 |
| Calcium propionate | 0.25 |
| Enzymes | as indicated below |

Sponge

Scaling of ingredients, addition of yeast, water, flour, SSL and oil into mixer bowl Mixing 90 rpm for 1 minutes, 150 rpm for 4 minutes The sponge was weighted, the temperature was measured and the sponge was placed in a bowl-fermentation 3 hours at 27 C, 86% RH Dough Addition of ingredients and the sponge into the mixer bowl. The sponge and ingredients were mixed together 90 rpm for 9 minutes The temperature was measured, dough characteristics were evaluated, the dough was scaled into smaller pieces of 435 g each.

The dough rests on the table for 10 minutes

Doughs were sheeted and molded.

Fermentation for 55 minutes at 42° C. and 86% RH.

Bread were baked at 200° C. for 22 minutes

Enzymes were dosed at 400 MANU/kg of Novamyl together with 0, 5 or 20 AmU/kg of the amylase of SEQ ID NO: 2 (prepared as in Example 1).

Bread were stored at room temperature until analysis.

Texture and water migration by NMR were measured on day 7, 14 and 21. A small sensory evaluation of softness and moistness was performed on day 21.

Results

Firmness of the loaves was measured as described in WO 9953769 The results were as follows:

| Novamyl dosage MANU/kg | Amylase of invention AmU/kg | Firmness after 7 days g | Firmness after 14 days g | Firmness after 21 days g |
|---|---|---|---|---|
| 400 | 0 | 593 | 869 | 1103 |
| 400 | 5 | 505 | 814 | 1000 |
| 400 | 20 | 480 | 789 | 939 |

Elasticity of the loaves was measured as described in U.S. Pat. No. 6,162,628. The results were as follows:

| Novamyl dosage MANU/kg | Amylase of invention AmU/kg | Elasticity after 7 days % | Elasticity after 14 days % | Elasticity after 21 days % |
|---|---|---|---|---|
| 400 | 0 | 50.7 | 46.5 | 45.2 |
| 400 | 5 | 50.1 | 46.7 | 44.7 |
| 400 | 20 | 50.7 | 47.2 | 46.0 |

The data show that the amylase of the invention has a significant effect on firmness in combination with Novamyl, furthermore the elasticity seems to be comparable to or even better than that of Novamyl after 21 days of storage.

The mobility of free water was determined as described by P. L. Chen, Z. Long, R. Ruan and T. P. Labuza, Nuclear Magnetic Resonance Studies of water Mobility in Bread during Storage. Lebensmittel Wissenschaft und Technologie 30, 178-183 (1997). The results were as follows:

| Novamyl dosage MANU/kg | Amylase of invention AmU/kg | Free water after 7 days Micro-sec | Free water after 14 days Micro-sec | Free water after 21 days Micro-sec |
|---|---|---|---|---|
| 400 | 0 | 7498 | 6921 | 6198 |
| 400 | 5 | 7780 | 6856 | 6424 |
| 400 | 20 | 7945 | 7004 | 6618 |

The data show that the amylase of the invention increases the amount of free water. The amount of free water has been described in literature to correlate to moistness of bread crumb.

The ranking from the small sensory evaluation of softness and moistness on day 21 showed the following ranking (MANU/kg of Novamyl+AmU/kg of amylase of invention):

Moistest: 400 MANU+20 AmU

Second: 400 MANU+5 AmU

Lowest (least moist): 400 MANU

The invention claimed is:

1. An isolated polypeptide which has amylase activity and has an amino acid sequence which comprises:
   a) a sequence having at least 90% identity to the catalytic core sequence of the amylase encoded by the DNA sequence inserted into the plasmid in *E. coli* DSM 16113;
   b) a sequence having at least 90% identity to the sequence as shown in positions 1-439 or positions 1-566 of SEQ ID NO: 2; or
   c) a sequence encoded by a nucleic acid sequence comprising the nucleotides 146-1462 of SEQ ID NO: 1.

2. The polypeptide of claim 1, comprising an amino acid sequence which has at least 95% identity with the sequence as shown in positions 1-439 or position 1-566 of SEQ ID NO 2.

3. The polypeptide of claim 1, comprising an amino acid sequence which has at least 98% identity with the sequence as shown in positions 1-439 or position 1-566 of SEQ ID NO 2.

4. The polypeptide of claim 1, consisting of the amino acid sequence as shown in positions 1-439 of SEQ ID NO: 2.

5. The polypeptide of claim 1, consisting of the amino acid sequence as shown in positions 1-566 of SEQ ID NO: 2.

6. The polypeptide of claim 1 wherein the amino acid sequence further comprises a carbohydrate-binding domain.

7. An isolated polynucleotide comprising a sequence which encodes the polypeptide of claim 1.

8. A vector comprising the polynucleotide of claim 7 operably linked to one or more control sequences that direct the production of the polypeptide in a suitable host.

9. An isolated transformed host cell comprising the vector of claim 8.

10. A method for producing an amylase, which comprises
   a) cultivating the host cell of claim 9 under conditions appropriate for expression of amylase, and
   b) recovering the amylase.

11. A dough composition which comprises flour and the polypeptide of claim 1.

12. A process for preparing a dough-based product, comprising adding the polypeptide of claim 1 to a dough, leavening, and heating the dough.

13. The process of claim 12 which further comprises adding an exo-acting amylase to the dough.

14. The process of claim 13 wherein the exo-acting amylase is a maltogenic alpha-amylase.

* * * * *

UNITED STATES PATENT AND TRADEMARK OFFICE
CERTIFICATE OF CORRECTION

PATENT NO. : 7,666,650 B2 Page 1 of 1
APPLICATION NO. : 10/585620
DATED : February 23, 2010
INVENTOR(S) : Ye et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 363 days.

Signed and Sealed this

Seventh Day of December, 2010

David J. Kappos
*Director of the United States Patent and Trademark Office*

SEQUENCE LISTING

```
<160> NUMBER OF SEQ ID NOS: 17

<210> SEQ ID NO 1
<211> LENGTH: 1946
<212> TYPE: DNA
<213> ORGANISM: Chaetomium sp.
<220> FEATURE:
<221> NAME/KEY: CDS
<222> LOCATION: (86)..(1843)
<220> FEATURE:
<221> NAME/KEY: sig_peptide
<222> LOCATION: (86)..(145)
```

-continued

```
<220> FEATURE:
<221> NAME/KEY: mat_peptide
<222> LOCATION: (146)..(1843)

<400> SEQUENCE: 1
tcccggtcat cctctcttgg tccctgccat cctcctgccc cctctgatcc accgcctctt    60
cggtggactc caagacgttg tcagg atg cga tcc ttc ctc gcc ctc tca gcc       112
                            Met Arg Ser Phe Leu Ala Leu Ser Ala
                            -20             -15 ttg ctg ctg ctg tac ccg ctg cag ctg ctc gcc gcc agc aac tcc gac      160
Leu Leu Leu Leu Tyr Pro Leu Gln Leu Leu Ala Ala Ser Asn Ser Asp
    -10              -5              -1  1                   5 tgg agg tcc cgc aat atc tac ttt gcc ttg acc gac cgc gtc gcc aat      208
Trp Arg Ser Arg Asn Ile Tyr Phe Ala Leu Thr Asp Arg Val Ala Asn
                10              15                      20 ccg tcc acc acg acc gca tgt agt gac ctg agc aac tac tgc ggc ggc      256
Pro Ser Thr Thr Thr Ala Cys Ser Asp Leu Ser Asn Tyr Cys Gly Gly
            25                  30                  35 acg tgg agc ggc ctg tcg agc aag ctg gac tac atc caa ggg atg ggc      304
Thr Trp Ser Gly Leu Ser Ser Lys Leu Asp Tyr Ile Gln Gly Met Gly
        40                  45                  50 ttc gat tcc atc tgg att acc ccc gtg gtc gag aac tgc gac ggt ggc      352
Phe Asp Ser Ile Trp Ile Thr Pro Val Val Glu Asn Cys Asp Gly Gly
    55                  60                  65 tac cac ggc tac tgg gcc aag gcg ctc tac aac gtc aac acg aac tac      400
Tyr His Gly Tyr Trp Ala Lys Ala Leu Tyr Asn Val Asn Thr Asn Tyr
70                  75                  80                  85 ggc agt gcg gat gat ctg aag aac ttc gtt gcg gcc gcc cat gcg aag      448
Gly Ser Ala Asp Asp Leu Lys Asn Phe Val Ala Ala Ala His Ala Lys
                90                  95                  100 ggc atg tac gtg atg gtg gac gtc gtc gcg aat cac atg ggt tcc tgc      496
Gly Met Tyr Val Met Val Asp Val Val Ala Asn His Met Gly Ser Cys
            105                 110                 115 ggc atc gcc aac ctc tcc cca cct ccc ctg aac gag cag agc tct tat      544
Gly Ile Ala Asn Leu Ser Pro Pro Pro Leu Asn Glu Gln Ser Ser Tyr
        120                 125                 130 cac acc cag tgc gac att gac tac agc agt cag tcc agc att gag acg      592
His Thr Gln Cys Asp Ile Asp Tyr Ser Ser Gln Ser Ser Ile Glu Thr
    135                 140                 145 tgc tgg ata tcc ggc ctc cct gac ctg gac acc acc gat agc act atc      640
Cys Trp Ile Ser Gly Leu Pro Asp Leu Asp Thr Thr Asp Ser Thr Ile
150                 155                 160                 165 cga tcc ctc ttc cag acc tgg gtc cac ggc ctg gtc agc aac tac agc      688
Arg Ser Leu Phe Gln Thr Trp Val His Gly Leu Val Ser Asn Tyr Ser
                170                 175                 180 ttc gac ggt ctc cgc gtc gac acc gtc aag cac gtg gag aag gat tac      736
Phe Asp Gly Leu Arg Val Asp Thr Val Lys His Val Glu Lys Asp Tyr
            185                 190                 195 tgg ccc ggc ttc gtg tcg gcg gcg ggc acc tac gcc atc ggc gaa gtc      784
Trp Pro Gly Phe Val Ser Ala Ala Gly Thr Tyr Ala Ile Gly Glu Val
        200                 205                 210 ttc tcc ggc gac acc tcc tac gtg gcc ggc tat caa tcg gtg atg ccg      832
Phe Ser Gly Asp Thr Ser Tyr Val Ala Gly Tyr Gln Ser Val Met Pro
    215                 220                 225 ggc ttg ctc aac tat ccc atc tac tat ccg ctc atc cgc gtc ttc gcg      880
Gly Leu Leu Asn Tyr Pro Ile Tyr Tyr Pro Leu Ile Arg Val Phe Ala
230                 235                 240                 245 cag ggt gcg tcc ttc acc gat ctc gtc aac aac cac gat acc gtc ggc      928
Gln Gly Ala Ser Phe Thr Asp Leu Val Asn Asn His Asp Thr Val Gly
                250                 255                 260
```

| | |
|---|---|
| tcg acc ttc tcc gac ccg acg ctg ctg ggt aac ttt atc gac aac cac<br>Ser Thr Phe Ser Asp Pro Thr Leu Leu Gly Asn Phe Ile Asp Asn His<br>        265                  270                  275 | 976 |
| gac aac cca cgt ttc ctg agc tac acc agc gac cac gcc ctc ctc aag<br>Asp Asn Pro Arg Phe Leu Ser Tyr Thr Ser Asp His Ala Leu Leu Lys<br>280                  285                  290 | 1024 |
| aac gct ctg gcc tac gtc atc ctg gcc aga ggc atc ccc atc gtc tac<br>Asn Ala Leu Ala Tyr Val Ile Leu Ala Arg Gly Ile Pro Ile Val Tyr<br>        295                  300                  305 | 1072 |
| tac ggc acc gag caa ggc tac tcg ggt tcg tcc gac ccg gcg aac cgc<br>Tyr Gly Thr Glu Gln Gly Tyr Ser Gly Ser Ser Asp Pro Ala Asn Arg<br>310                  315                  320                  325 | 1120 |
| gag gat ctc tgg cgt agc gga tac agc act acg gga gac atc tac acc<br>Glu Asp Leu Trp Arg Ser Gly Tyr Ser Thr Thr Gly Asp Ile Tyr Thr<br>                  330                  335                  340 | 1168 |
| acc atc gcc gcg ctc tcc gcc gcg cgc acc gcg gcc ggt ggc ctc gcc<br>Thr Ile Ala Ala Leu Ser Ala Ala Arg Thr Ala Ala Gly Gly Leu Ala<br>        345                  350                  355 | 1216 |
| ggt aac gac cac gtc cac ctg tac acg acc gac aac gcg tac gcc tgg<br>Gly Asn Asp His Val His Leu Tyr Thr Thr Asp Asn Ala Tyr Ala Trp<br>360                  365                  370 | 1264 |
| tcc cgg gcg agc ggc aag ctc atc gtc gtc acg tcc aac cgc ggc agc<br>Ser Arg Ala Ser Gly Lys Leu Ile Val Val Thr Ser Asn Arg Gly Ser<br>        375                  380                  385 | 1312 |
| tcc gac agc agc acc atc tgc ttc agc acc cag cag gcc agc ggc acc<br>Ser Asp Ser Ser Thr Ile Cys Phe Ser Thr Gln Gln Ala Ser Gly Thr<br>390                  395                  400                  405 | 1360 |
| acc tgg acc agc acg atc acc ggc aac tcg tac acc gcc gac agc aac<br>Thr Trp Thr Ser Thr Ile Thr Gly Asn Ser Tyr Thr Ala Asp Ser Asn<br>                  410                  415                  420 | 1408 |
| ggc cag atc tgc gtg cag ctg tcc agc ggc gga ccc gag gcg ctc gtc<br>Gly Gln Ile Cys Val Gln Leu Ser Ser Gly Gly Pro Glu Ala Leu Val<br>        425                  430                  435 | 1456 |
| gtc tcc acc gcg acc ggc acc gcc acc gcg acg act ctg tcc acg acc<br>Val Ser Thr Ala Thr Gly Thr Ala Thr Ala Thr Thr Leu Ser Thr Thr<br>440                  445                  450 | 1504 |
| acc aag acg tcc acc tcg acc gcc tcc tgc gcc gcc acc gtc gcc gtc<br>Thr Lys Thr Ser Thr Ser Thr Ala Ser Cys Ala Ala Thr Val Ala Val<br>        455                  460                  465 | 1552 |
| acc ttc aac gag ctc gtc acc acg aac tac ggc gac acc atc cgc ctg<br>Thr Phe Asn Glu Leu Val Thr Thr Asn Tyr Gly Asp Thr Ile Arg Leu<br>470                  475                  480                  485 | 1600 |
| acg ggc tcc atc tcc cag ctc agc agc tgg agc gca acc tcg ggg ctg<br>Thr Gly Ser Ile Ser Gln Leu Ser Ser Trp Ser Ala Thr Ser Gly Leu<br>                  490                  495                  500 | 1648 |
| gcc ctg agc gcg tcc gcg tac acg tcc agc aac ccg ctc tgg agc gtg<br>Ala Leu Ser Ala Ser Ala Tyr Thr Ser Ser Asn Pro Leu Trp Ser Val<br>        505                  510                  515 | 1696 |
| acg gtc agc ctg ccg gcc ggc acg tcg ttc gag tac aag ttc gtc cgc<br>Thr Val Ser Leu Pro Ala Gly Thr Ser Phe Glu Tyr Lys Phe Val Arg<br>520                  525                  530 | 1744 |
| atc acg agc gac ggc acc gtg acc tgg gaa tcg gac ccg aac cgc agc<br>Ile Thr Ser Asp Gly Thr Val Thr Trp Glu Ser Asp Pro Asn Arg Ser<br>        535                  540                  545 | 1792 |
| tac acc gtc ccg acg tgc gcg agc acc gcg acg atc agc aat acc tgg<br>Tyr Thr Val Pro Thr Cys Ala Ser Thr Ala Thr Ile Ser Asn Thr Trp<br>550                  555                  560                  565 | 1840 |

```
cgg tgagctctgg acgtgttgta catataggag gccgttgaga ggccggggcg              1893
Arg gttggtggtc ggggtgaatg gggggttgat gcttttcgt tgtgtcggtg aga              1946
```

<210> SEQ ID NO 2
<211> LENGTH: 586
<212> TYPE: PRT
<213> ORGANISM: Chaetomium sp.

<400> SEQUENCE: 2

```
Met Arg Ser Phe Leu Ala Leu Ser Ala Leu Leu Leu Tyr Pro Leu
-20             -15                 -10                 -5

Gln Leu Leu Ala Ala Ser Asn Ser Asp Trp Arg Ser Arg Asn Ile Tyr
        -1  1               5                   10

Phe Ala Leu Thr Asp Arg Val Ala Asn Pro Ser Thr Thr Ala Cys
            15                  20                  25

Ser Asp Leu Ser Asn Tyr Cys Gly Gly Thr Trp Ser Gly Leu Ser Ser
        30                  35                  40

Lys Leu Asp Tyr Ile Gln Gly Met Gly Phe Ser Ile Trp Ile Thr
45              50                  55                  60

Pro Val Val Glu Asn Cys Asp Gly Gly Tyr His Gly Tyr Trp Ala Lys
                65                  70                  75

Ala Leu Tyr Asn Val Asn Thr Asn Tyr Gly Ser Ala Asp Asp Leu Lys
            80                  85                  90

Asn Phe Val Ala Ala Ala His Ala Lys Gly Met Tyr Val Met Val Asp
            95                  100                 105

Val Val Ala Asn His Met Gly Ser Cys Gly Ile Ala Asn Leu Ser Pro
        110                 115                 120

Pro Pro Leu Asn Glu Gln Ser Ser Tyr His Thr Gln Cys Asp Ile Asp
125                 130                 135                 140

Tyr Ser Ser Gln Ser Ser Ile Glu Thr Cys Trp Ile Ser Gly Leu Pro
            145                 150                 155

Asp Leu Asp Thr Thr Asp Ser Thr Ile Arg Ser Leu Phe Gln Thr Trp
            160                 165                 170

Val His Gly Leu Val Ser Asn Tyr Ser Phe Asp Gly Leu Arg Val Asp
        175                 180                 185

Thr Val Lys His Val Glu Lys Asp Tyr Trp Pro Gly Phe Val Ser Ala
        190                 195                 200

Ala Gly Thr Tyr Ala Ile Gly Glu Val Phe Ser Gly Asp Thr Ser Tyr
205                 210                 215                 220

Val Ala Gly Tyr Gln Ser Val Met Pro Gly Leu Leu Asn Tyr Pro Ile
            225                 230                 235

Tyr Tyr Pro Leu Ile Arg Val Phe Ala Gln Gly Ala Ser Phe Thr Asp
            240                 245                 250

Leu Val Asn Asn His Asp Thr Val Gly Ser Thr Phe Ser Asp Pro Thr
            255                 260                 265

Leu Leu Gly Asn Phe Ile Asp Asn His Asp Asn Pro Arg Phe Leu Ser
            270                 275                 280

Tyr Thr Ser Asp His Ala Leu Leu Lys Asn Ala Leu Ala Tyr Val Ile
285                 290                 295                 300

Leu Ala Arg Gly Ile Pro Ile Val Tyr Tyr Gly Thr Glu Gln Gly Tyr
            305                 310                 315

Ser Gly Ser Ser Asp Pro Ala Asn Arg Glu Asp Leu Trp Arg Ser Gly
            320                 325                 330
```

Tyr Ser Thr Thr Gly Asp Ile Tyr Thr Thr Ile Ala Ala Leu Ser Ala
            335                 340                 345

Ala Arg Thr Ala Ala Gly Gly Leu Ala Gly Asn Asp His Val His Leu
        350                 355                 360

Tyr Thr Thr Asp Asn Ala Tyr Ala Trp Ser Arg Ala Ser Gly Lys Leu
365                 370                 375                 380

Ile Val Val Thr Ser Asn Arg Gly Ser Ser Asp Ser Ser Thr Ile Cys
            385                 390                 395

Phe Ser Thr Gln Gln Ala Ser Gly Thr Thr Trp Thr Ser Thr Ile Thr
            400                 405                 410

Gly Asn Ser Tyr Thr Ala Asp Ser Asn Gly Gln Ile Cys Val Gln Leu
            415                 420                 425

Ser Ser Gly Gly Pro Glu Ala Leu Val Val Ser Thr Ala Thr Gly Thr
        430                 435                 440

Ala Thr Ala Thr Thr Leu Ser Thr Thr Thr Lys Thr Ser Thr Ser Thr
445                 450                 455                 460

Ala Ser Cys Ala Ala Thr Val Ala Val Thr Phe Asn Glu Leu Val Thr
                465                 470                 475

Thr Asn Tyr Gly Asp Thr Ile Arg Leu Thr Gly Ser Ile Ser Gln Leu
            480                 485                 490

Ser Ser Trp Ser Ala Thr Ser Gly Leu Ala Leu Ser Ala Ser Ala Tyr
        495                 500                 505

Thr Ser Ser Asn Pro Leu Trp Ser Val Thr Val Ser Leu Pro Ala Gly
            510                 515                 520

Thr Ser Phe Glu Tyr Lys Phe Val Arg Ile Thr Ser Asp Gly Thr Val
525                 530                 535                 540

Thr Trp Glu Ser Asp Pro Asn Arg Ser Tyr Thr Val Pro Thr Cys Ala
                545                 550                 555

Ser Thr Ala Thr Ile Ser Asn Thr Trp Arg
            560                 565

<210> SEQ ID NO 3
<211> LENGTH: 18
<212> TYPE: DNA
<213> ORGANISM: Artificial
<220> FEATURE:
<223> OTHER INFORMATION: Primer amyD1
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 3
gsntaccayg gntactgg                                                 18

<210> SEQ ID NO 4
<211> LENGTH: 17
<212> TYPE: DNA
<213> ORGANISM: Artificial
<220> FEATURE:
<223> OTHER INFORMATION: Primer amyD2R
<220> FEATURE:
<221> NAME/KEY: misc_feature
<222> LOCATION: (15)..(15)
<223> OTHER INFORMATION: n is a, c, g, or t

```
<400> SEQUENCE: 4
tarayratkg gratncc                                                    17

<210> SEQ ID NO 5
<211> LENGTH: 17
<212> TYPE: DNA
<213> ORGANISM: Artificial
<220> FEATURE:
<223> OTHER INFORMATION: Primer AM835n-s1
<220> FEATURE:
<221> NAME/KEY: misc_feature
<222> LOCATION: (15)..(15)
<223> OTHER INFORMATION: n is a, c, g, or t

<400> SEQUENCE: 5
aayaartayt tygcnyt                                                    17

<210> SEQ ID NO 6
<211> LENGTH: 17
<212> TYPE: DNA
<213> ORGANISM: Artificial
<220> FEATURE:
<223> OTHER INFORMATION: Primer AM835n-s2a
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 6
ctnggngaya grgtngc                                                    17

<210> SEQ ID NO 7
<211> LENGTH: 17
<212> TYPE: DNA
<213> ORGANISM: Artificial
<220> FEATURE:
<223> OTHER INFORMATION: Primer AM835n-s2b
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 7
ctnggngayc grgtngc                                                    17

<210> SEQ ID NO 8
<211> LENGTH: 17
<212> TYPE: DNA
<213> ORGANISM: Artificial
<220> FEATURE:
<223> OTHER INFORMATION: Primer AM835n-s2c
<220> FEATURE:
<221> NAME/KEY: misc_feature
<222> LOCATION: (3)..(3)
<223> OTHER INFORMATION: n is a, c, g, or t
```

-continued

```
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 8
ctnggngayc gygtngc                                                  17

<210> SEQ ID NO 9
<211> LENGTH: 18
<212> TYPE: DNA
<213> ORGANISM: Artificial
<220> FEATURE:
<223> OTHER INFORMATION: amy835as1

<400> SEQUENCE: 9
gcggatagta gatgggat                                                 18

<210> SEQ ID NO 10
<211> LENGTH: 17
<212> TYPE: DNA
<213> ORGANISM: Artificial
<220> FEATURE:
<223> OTHER INFORMATION: Primer amy835f2

<400> SEQUENCE: 10
gtgcgtcctt caccgat                                                  17

<210> SEQ ID NO 11
<211> LENGTH: 17
<212> TYPE: DNA
<213> ORGANISM: Artificial
<220> FEATURE:
<223> OTHER INFORMATION: amy835s00

<400> SEQUENCE: 11
tcccgtcatc ctctctt                                                  17

<210> SEQ ID NO 12
<211> LENGTH: 18
<212> TYPE: DNA
<213> ORGANISM: Artificial
<220> FEATURE:
<223> OTHER INFORMATION: amy835as01

<400> SEQUENCE: 12
tctcaccgac acaacgaa                                                 18

<210> SEQ ID NO 13
<211> LENGTH: 20
<212> TYPE: PRT
<213> ORGANISM: Chaetomium sp.
<220> FEATURE:
<221> NAME/KEY: misc_feature
<222> LOCATION: (9)..(9)
<223> OTHER INFORMATION: Xaa can be any naturally occurring amino acid

<400> SEQUENCE: 13

Ala Ser Asn Ser Asp Trp Arg Ser Xaa Asn Lys Tyr Phe Ala Leu Gly
1               5                   10                  15

Asp Arg Val Ala
            20
```

```
<210> SEQ ID NO 14
<211> LENGTH: 17
<212> TYPE: DNA
<213> ORGANISM: Artificial
<220> FEATURE:
<223> OTHER INFORMATION: amy835as3

<400> SEQUENCE: 14
gtagtcaatg tcgcact                                                   17

<210> SEQ ID NO 15
<211> LENGTH: 18
<212> TYPE: DNA
<213> ORGANISM: Artificial
<220> FEATURE:
<223> OTHER INFORMATION: amy835f1

<400> SEQUENCE: 15
ccatctacta tccgctca                                                  18

<210> SEQ ID NO 16
<211> LENGTH: 28
<212> TYPE: DNA
<213> ORGANISM: Artificial
<220> FEATURE:
<223> OTHER INFORMATION: Primer AM835.1

<400> SEQUENCE: 16
ccaggatccg tcaggatgcg atccttcc                                       28

<210> SEQ ID NO 17
<211> LENGTH: 29
<212> TYPE: DNA
<213> ORGANISM: Artificial
<220> FEATURE:
<223> OTHER INFORMATION: Primer AM835.2

<400> SEQUENCE: 17
cgtctcgagg acacaacgaa aaagcatca                                      29
```